US00PP24037P3

(12) United States Plant Patent
Klemm et al.

(10) Patent No.: US PP24,037 P3
(45) Date of Patent: Nov. 19, 2013

(54) ***LOBELIA* PLANT NAMED 'KLELE11769'**

(50) Latin Name: *Lobelia erinus*
Varietal Denomination: KLELE11769

(75) Inventors: Nils Klemm, Stuttgart (DE); Guido Von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 42 days.

(21) Appl. No.: 13/506,046

(22) Filed: Mar. 22, 2012

(65) Prior Publication Data

US 2013/0254962 P1 Sep. 26, 2013

(51) Int. Cl.
*A01H 5/00* (2006.01)

(52) U.S. Cl.
USPC ..... Plt./451

(58) Field of Classification Search
USPC ..... Plt./451
See application file for complete search history.

*Primary Examiner* — Kent L Bell
(74) *Attorney, Agent, or Firm* — Jondle Plant Sciences Division of Swanson & Bratschun, L.L.C.

(57) ABSTRACT

A new *lobelia* plant named 'KLELE11769' particularly distinguished by its flat vigorous growing habit, white flowers, and strong dark green foliage, is disclosed.

1 Drawing Sheet

Genus and species: *Lobelia erinus*.
Variety denomination: 'KLELE11769'.

BACKGROUND OF THE NEW PLANT

The present invention comprises a new and distinct variety of *lobelia*, botanically known as *Lobelia erinus*, and hereinafter referred to by the variety name 'KLELE11769'. The new variety resulted from a controlled cross conducted in June 2006 in Stuttgart, Germany, between female parent *lobelia* plant named 'LE 06 0159', (unpatented) and male parent *lobelia* plant named 'LE 08 0114' (unpatented). A single plant selection was subsequently chosen for further evaluation and asexual propagation.

The new variety was first propagated via vegetative cuttings and in vitro propagation in May 2007 in Stuttgart, Germany, and has been asexually reproduced repeatedly by vegetative cuttings for 10 generations. 'KLELE11769' has been found to retain its distinctive characteristics through successive asexual propagations via vegetative cuttings.

Plant Breeder's Rights for this variety were applied for in Canada on Mar. 4, 2011. 'KLELE11769' has not been made publicly available more than one year prior to filing of this application.

SUMMARY OF THE INVENTION

The following are the most outstanding and distinguishing characteristics of this new cultivar when grown under normal horticultural practices in a glass greenhouse in Stuttgart, Germany.

1. Flat vigorous growth;
2. White flowers; and
3. Strong, dark green foliage.

DESCRIPTION OF PHOTOGRAPH

This new *lobelia* plant is illustrated by the accompanying photograph which shows overall plant habit including blooms, buds, and foliage of the plant in full color. The colors shown are as true as can be reasonably obtained by conventional photographic procedures. The photograph was taken in Spring of 2011 of a 3-month old *lobelia* plant grown in a 10 centimeter pot in a glass greenhouse in Stuttgart, Germany under normal horticultural practices.

DESCRIPTION OF THE NEW VARIETY

The following detailed descriptions set forth the distinctive characteristics of 'KLELE11769'. The data which define these characteristics were collected from asexual reproductions carried out in Stuttgart, Germany. The plant history was taken in the Spring of 2011 of 3-month old plants grown in 10 centimeter pots in a glass greenhouse with a minimum pinch date of eight weeks. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Botanical.*—*Lobelia erinus.*
- *Common name.*—*Lobelia.*
- *Designation.*—'KLELE11769'.

Parentage:
- *Female parent.*—*Lobelia* plant named 'LE 06 0159' (unpatented).
- *Male parent.*—*Lobelia* plant named 'LE 08 0114' (unpatented).

Growth:
- *Growth and branching habit.*—Half-hanging.
- *Form.*—Rounded to flat.
- *Height* (*measured from the top of the soil, including any flowers*).—6.0 cm.
- *Width* (*horizontal plant diameter, including any flowers*).—18.0 cm to 20.0 cm.
- *Time to produce a finished flowering plant.*—10 weeks.
- *Outdoor plant performance.*—Very good.
- *Time to initiate roots.*—3 weeks.

*Root description*.—Fine, white roots, freely branching and dense.

Leaves:

*Arrangement*.—Alternate.

*Color* (*immature and mature leaves*).—Upper surface: RHS N137C. Lower surface: RHS 138B.

*Basal*.—Length: 2.0 cm to 3.0 cm. Width: 0.7 cm to 0.8 cm. Shape: Elliptical to rounded. Margin: Serrate. Apex: Obtuse. Base: Acute. Texture (both surfaces): Smooth. Venation: Pinnate. Venation color: Upper surface: RHS 142B. Lower surface: RHS N137C.

*Upper*.—Length: 0.5 cm to 1.0 cm. Width: 0.3 cm to 0.7 cm. Shape: Elliptical. Margin: Serrate. Apex: Obtuse. Base: Acute. Texture (both surfaces): Smooth. Venation: Pinnate. Venation color: Upper surface: RHS 142B. Lower surface: RHS N137C.

Stems:

*Length*.—Approximately 12.0 cm to 13.0 cm.

*Diameter*.—0.2 cm to 0.3 cm.

*Internode length*.—1.5 cm to 1.8 cm.

*Color*.—RHS 137B.

*Texture*.—Smooth.

*Stem anthocyanin*.—Absent.

*Peduncle*.—Color: RHS 143A. Length: Approximately 2.0 cm. Diameter: 0.1 cm. Texture: Smooth.

*Pedicel*.—Length: 1.5 cm to 2.0 cm. Diameter: 0.08 cm. Color: RHS 143A.

Flower buds:

*Color* (*when first opening*).—Yellow at the top; greenish white at the bottom.

*Shape*.—Inverse drop.

*Diameter*.—0.4 cm.

*Length*.—0.8 cm.

Inflorescence:

*Blooming habit*.—Continuous.

*Natural flowering season*.—Early spring until mid-summer.

*Lastingness of individual blooms on plant*.—Approximately 1 week.

*Fragrance*.—Absent.

*Inflorescence type*.—Raceme.

*Quantity of flowers and buds per flowering branch*.—10 to 15.

*Inflorescence height*.—10.0 cm to 20.0 cm.

*Inflorescence diameter*.—4.0 cm.

*Note*.—Inflorescence represents approximately ¾ of each branch.

Flowers:

*Arrangement*.—5 lobes; 3 lower and 2 upper.

*Flower diameter* (*horizontal*).—Approximately 2.0 cm.

*Flower height* (*vertical*).—Approximately 1.0 cm.

*Immature flower*.—Upper lobes color: Upper surface: More white than RHS NN155D. Lower surface: More white than RHS NN155D. Lower lobes color: Upper surface: More white than RHS NN155D. Lower surface: More white than RHS NN155D.

*Mature flower*.—Upper lobes: Color: Upper surface: More white than RHS NN155D. Lower surface: More white than RHS NN155D. Length: Approximately 1.2 cm. Width: Approximately 0.7 cm. Shape: Obovate. Apex: Obtuse. Margin: Entire. Texture (both surfaces): Smooth. Lower lobes: Color: Upper surface: RHS NN155D. Lower surface: RHS NN155D. Length: Approximately 0.4 cm. Width: Approximately 0.2 cm. Shape: Obovate. Apex: Obtuse. Margin: Entire. Texture (both surfaces): Smooth.

*Corolla*.—Color inside: RHS NN155D with two yellow elongated spots (RHS 2B). Color outside: RHS NN155D. Tube length: 0.9 cm. Diameter: 0.2 cm at the top.

*Calyx*.—Sepals: 5. Sepal margin: Entire. Color (both surfaces): RHS 143A. Length: Approximately 0.6 cm. Diameter: Approximately 0.1 cm. Shape: Funnel, star-shaped with fused sepals in lower half. Apex: Acute. Texture (both surfaces): Smooth.

Reproductive organs:

*Androecium*.—Quantity of anthers: 5. Anther length: 0.25 cm to 0.30 cm. Anther width: 0.1 cm to 0.12 cm. Anther color: RHS 164C. Filament length: Approximately 0.5 cm. Filament color: White (RHS N155D). Pollen amount: Sparse. Pollen color: RHS 164C.

*Gynoecium*.—Pistil number: 1. Pistil length: Approximately 0.4 cm. Stigma shape: Reniform. Stigma color: Bluish grey (RHS N187D). Style length: Approximately 0.3 cm. Style color: RHS NN155D.

Fruit and seed set: None observed.

Disease and insect resistance: None tested.

COMPARISON WITH PARENTAL AND COMMERCIAL VARIETIES

'KLELE11769' differs from the female parent, 'LE 06 0129', (unpatented) in that 'KLELE11769' has very good branching with a stable habit, whereas 'LE 06 0129' has moderate branching and a loose habit.

'KLELE11769' differs from the male parent, 'LE 08 0114', (unpatented) in that 'KLELE11769' has strong branches and bigger flowers, whereas 'LE 08 0114' has soft branches and smaller flowers.

'KLELE11769' differs from the commercial variety 'KLELE06115' (U.S. Plant Pat. No. 19,693) in that 'KLELE11769' has flat growth and a medium early flowering date, whereas 'KLELE06115' has mounding to semi-trailing growth and very late flowering.

We claim:

1. A new and distinct *lobelia* plant named 'KLELE11769' as shown and described herein.

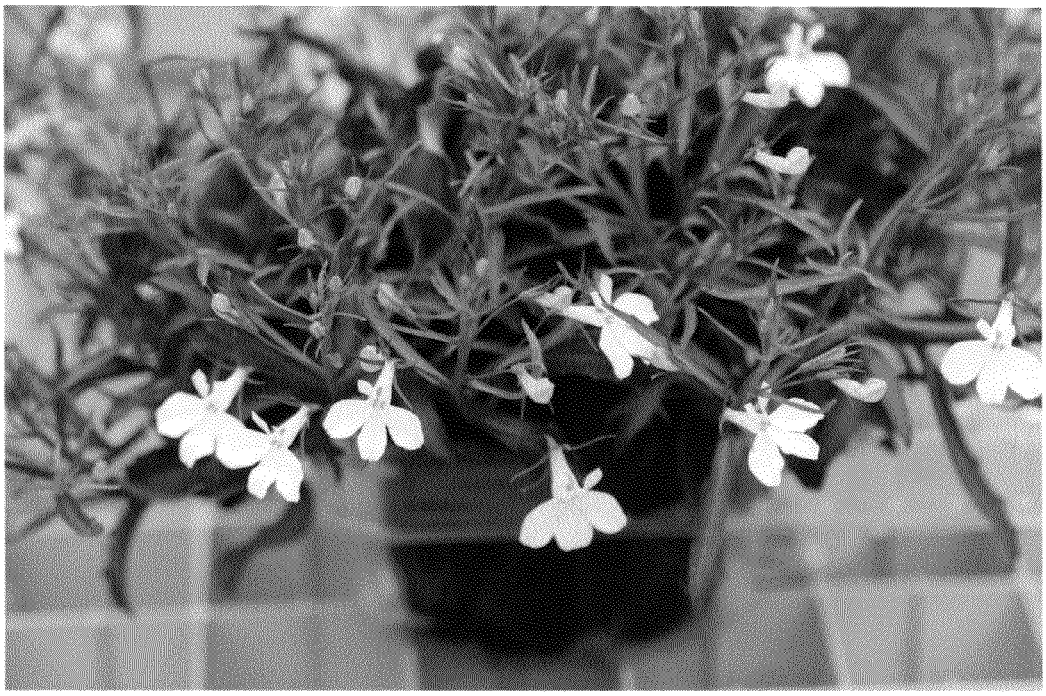

* * * * *